United States Patent [19]

Chastain et al.

[11] Patent Number: 5,153,229

[45] Date of Patent: Oct. 6, 1992

[54] PROCESS FOR PRODUCING REFERENCE BACTERICIDAL ENDPOINT (RBE) LIMONENE

[75] Inventors: Doyle E. Chastain, 137 Birch St., Titusville, Fla. 32780; W. Eugene Sanders, Jr.; Christine C. Sanders, both of Omaha, Nebr.

[73] Assignee: Doyle E. Chastain, Titusville, Fla.

[21] Appl. No.: 531,570

[22] Filed: Jun. 1, 1990

[51] Int. Cl.$^5$ .................... A01N 27/00; A01N 35/00
[52] U.S. Cl. .................... 514/763; 514/475; 514/690; 514/675; 514/739; 549/532; 568/377; 568/577; 568/822; 568/823; 568/825; 568/826; 568/828
[58] Field of Search ............... 514/475, 690, 675, 739, 514/763; 549/532; 568/377, 577, 822, 823, 825, 826, 828

[56] References Cited

U.S. PATENT DOCUMENTS

| | | | |
|---|---|---|---|
| Re. 28,263 | 12/1974 | Gauvreau | 514/358 |
| 2,152,003 | 10/1936 | van Peski et al. | 514/475 |
| 2,302,468 | 3/1941 | Palmer et al. | 514/690 |
| 2,863,882 | 12/1958 | Balin et al. | 514/179 |
| 3,014,047 | 12/1961 | Balin et al. | 549/512 |

OTHER PUBLICATIONS

Zuckerman, I. "Effect of Oxidized d-Limonene on Micro-Organisms", Nature, No. 4273, Sep. 22, 1951, p. 517.

Blumann et al. "Autoxidation of Limonene" J. Chem. Soc. 1965 (Apr.) 2990: Abstracted in Chemical Abstracts, vol. 63, 1965, p. 1819.

Kurita, N. and Koike S. "Synergistic Antimicrobial Effect of Acetic Acid Sodium Chloride and Essential Oil Components". Agricultural and Biological Chemistry, vol. 46(6), 1982; pp. 1655–1660: Abstracted in Biosis [Database] Biosis No. 75071998.

*Primary Examiner*—Allen J. Robinson
*Assistant Examiner*—John D. Pak
*Attorney, Agent, or Firm*—Arthur G. Yeager

[57] ABSTRACT

A process for producing a stable, bactericidal and fungicidal composition which consists essentially of bubbling air or oxygen into limonene, to produce an oxidized limonene having a rapid bactericidal activity as evidenced by the capability of killing at least 99.99% of the bacteria in a suitable culture medium inoculated with $10^6$ colony forming units of *Staphylococcus aureus* ATCC 25923 per ml.

12 Claims, No Drawings

PROCESS FOR PRODUCING REFERENCE BACTERICIDAL ENDPOINT (RBE) LIMONENE

TECHNICAL FIELD

The object of this invention is to show an economical process of producing oxidized limonene which has a potent, rapidly acting antimicrobial activity that persists when stored, and which is superior in antimicrobial activity to that of auto-oxidized limonene.

BACKGROUND OF THE INVENTION

1. Field of the Invention

During the study of fresh limonene as a hand cleaner, the applicants found that fresh limonene is an excellent solvent, but it is not bactericidal. Conversely, limonene which has undergone auto-oxidation, unexpectedly, was found to have a minimal, inconsistent antibacterial activity which varied in potency from batch to batch. Therefore, it was decided to purposely oxidize limonene to try to enhance and stabilize the antimicrobial properties of the limonene.

The applicants found that by bubbling air (or oxygen) into limonene to purposely oxidize (or oxygenate limonene which is the same) the oil, that it became bactericidal at progressively decreasing concentrations until it reached a point beyond which further oxidation caused a decrease in its bactericidal activity. As the purposeful oxidation of limonene progressed, it was noted that the physical properties of the limonene changed as its antimicrobial activity increased. Limonene, which was purposely oxidized was found to be effective in killing bacteria, yeasts, and fungi and its antimicrobial activity persisted unchanged when the purposely oxidized limonene was stored at 2°–4° C. in the dark, for periods exceeding one year.

The ability to produce limonene with a stable antimicrobial activity was unexpected and is not appreciated nor delineated in the prior art. In fact it is recognized in the prior art that the addition of air (or oxygen) to terpenes produces volatile mixtures of oxides and peroxides that are unstable. Limonene which undergoes auto-oxidation has an inconsistent antibacterial effect that is not rapidly bactericidal. It evaporates to a thick, non-usable gel before it becomes an effective antimicrobial when auto-oxidation is allowed to occur over a large surface area of the oil. On the other hand, limonene that is purposely oxidized becomes an excellent, stable bactericide and fungicide that is bactericidal and fungicidal in bactericidal and fungicidal concentrations and its activity can be demonstrated with even short interval application.

Thus, the object of this invention is to economically produce oxidized limonene: (1) with a potent, rapidly acting antimicrobial activity, (2) that will retain its antimicrobial activity when stored, and (3) that is superior in its antimicrobial activity to the antimicrobial activity of auto-oxidized limonene.

Limonene is a terpene with the following formula:

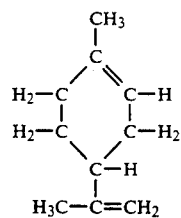

d-limonene

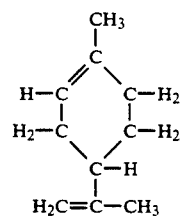

l-limonene

Limonene is an oil with a terpenic aroma. It is soluble in alcohol and miscible in oil, but it is insoluble in glycerine. Limonene is usually derived from either a pine or citrus origin. The l-isomer is derived from pine and has a characteristic pine aroma while the d-isomer is derived from citrus and has a characteristic citrus aroma. The l-isomer is also made synthetically, but the synthetic l-limonene has no characteristic aroma.

Commercial limonene is usually obtained from the peel of citrus fruit. Pressed liquor is obtained from the peel of any citrus fruit, but most commonly from oranges and grapefruit, after which it is passed through a flash evaporation at 240° F. at atmospheric conditions. Limonene is collected from the condensation of the flash vaporization. Limonene is used commercially as a flavoring agent, is used in large quantities to produce carvone which has a spearmint flavor, is used as a solvent, can be used as a base for soap or perfume, is used in the manufacture of rubber, and is useful as a penetrating oil.

Limonene undergoes auto-oxidation when it is exposed to air or oxygen. After exposure to air at room temperature, limonene becomes rancid with a foul smelling odor. The temperature has to be above about 40° F. for auto-oxidation to occur while temperatures above 90° F. increase the rate of evaporation. Because auto-oxidation limits the commercial value of limonene by causing it to become rancid with a foul smelling odor, limonene is usually stored in 55 gallon drums that have their interior painted with phenolic resin base enamel especially formulated for terpenes. The drums are completely filled and capped in order to limit exposure to air (and oxygen) that causes auto-oxidation. Auto-oxidized limonene develops antibacterial activity during auto-oxidation but does not become a rapidly acting bactericide. Auto-oxidation does not produce the potent, rapidly bactericidal limonene described in this patent.

2. Description of the prior art

The oxidation of limonene produces several chemical compounds that have been enumerated by several different investigators. For instance Bain (in U.S. Pat. No. 2,863,882 and 3,014,047) showed a method of producing and recovering terpenic oxidation products in which he delineated the oxidation products of limonene as: limonene-1,2-oxide, limonene-8,9-oxide, 1-menthene-9-ol, α-2,8-p-menthadiene-1-ol, β-2,8-p-menthadiene-1-ol, dihydrocarvone, β-cymenol, carvone, cis-carveol, and trans-carveol. He never studied the antimicrobial activity of oxidized limonene nor oxidized limonene to the point that it became stable with a potent antimicrobial activity. In fact, because limonene is chemically unstable during its oxidation, Bain thought that in order to obtain the maximum number of oxidation products from limonene, that he should add alkali to limonene when the peroxide value was between 1000 and 2000 and should cease adding air or oxygen to limonene. He thought the peroxide value was the sole indicator of the formation of limonene oxidation products (oxides and peroxides) and that these products could be obtained only when the oxidation of limonene was stopped as the peroxide value rose to its maximum. He never realized that the maximal activity achievable through the oxidation of limonene is obtained before maximum peroxide formation occurs.

Blumann listed the compounds formed by the auto-oxidation of limonene in Chemical Abstracts, Volume 63, 1965, n page 1819, and found minute amounts of cis and trans-carveol, trans-p-menth-8-ene-1,2-diol, limonene 1,2-epoxide, limonene 8,9-epoxide, cis and trans-p-mentha-2,8-dien-1-ol, and perillyl alcohol, but he never tried to purposely oxidize limonene and never tried to develop limonene with a stable, rapidly bactericidal activity.

Bardyshev studied the chemical compounds in photo-initiated, auto-oxidized, l-limonene and found tiny amounts of the following compounds: carvone, carveol, trans-p-menth-8-ene-1,2,-diol, hydroperoxide, p-menthane, p-cymene, terpinolene, p-mentha-2,4(8)-diene, cyclohexene, cuminic aldehyde, dihydrocarvone, piperitone, p-mentha-2,8-dien-1-ol, pulegone, carvomenthone, PhCOMe, 4-MeC$_6$H$_4$COMe, cyclohexanone, perillyl alcohol, and p-CH$_2$:CMeC$_6$H$_4$CH$_2$OH as was outlined in Chemical Abstracts, Volume 80, 1974, page 359. Like Blumann, Bardyshev never purposely oxidized limonene and never studied the antimicrobial activity of fresh nor auto-oxidized limonene.

Zuckerman studied the effect of d-limonene on bacteria and found that fresh limonene had no effect on bacteria. He found that when limonene became auto-oxidized, it developed minimal, inconsistent, weakly inhibitory (not bactericidal) properties. He noted that, at best, auto-oxidized limonene was only weakly inhibitory in that it only "shifts the time of the lag phase of bacterial growth without any influence on the logarithmic phase of bacterial growth." He noted that auto-oxidized limonene is unstable, and loses its inhibitory effect on keeping as was discussed in Nature 168: 517 (1951). He also recognized that the addition of alkali, as advocated by Bain in his method of oxidizing limonene, destroys the bacteriostatic properties of auto-oxidized limonene. He never recognized that limonene can be purposely oxidized to a point that it becomes a potent, stable antimicrobial which retains its antimicrobial activity when stored. In short, he could not make oxidized limonene with a stable, rapidly bactericidal activity.

In U.S. Pat. No. 3,595,975 Gauvreau showed a means of producing disinfecting compositions by combining cetyl pyridinium with terpenes to form antiseptics, but he never learned that limonene which had been purposely oxidized, becomes a potent, stable bactericide and fungicide. The active ingredient in his disinfecting compositions was cetyl pyridinium chloride (and not the terpenes).

DISCLOSURE OF THE INVENTION

This invention relates to an economical and safe process of producing oxidized limonene that has a potent, stable antimicrobial activity which is retained when it is stored. Its antimicrobial activity is superior to, and distinct from, the antimicrobial activity of auto-oxidized limonene. In one preferred use the oxidized limonene of this invention is a microbicide. Wherever used herein, the term "microbe" as used alone or in derivatives such as microbicide and antimicrobial, means a microscopic organism, such as bacteria, fungi, yeast, viruses, and rickettsia.

During the purposeful oxidation of limonene it was found that oxidized limonene became rapidly bactericidal as oxidation progressed. When the bactericidal activity of oxidized limonene: (a) became greater than that which could be accomplished by the auto-oxidation of limonene and, (b) could be demonstrated at a concentration of 0.06 or less against Staphylococcus aureus ATCC 25923 when incubated for sixty minutes, the oxidized limonene was defined as reference bactericidal endpoint limonene (i.e. RBE limonene). RBE limonene is a potent, stable, rapidly bactericidal compound.

The production of oxidized limonene that is bactericidal at a concentration of 0.06 or less against Staphylococcus aureus ATCC 25923 when incubated for sixty minutes can be produced by continuously bubbling air (method one) or oxygen (method two) through limonene at room temperature for three to eight weeks. The applicants prefer to bubble air into limonene because oxygen is more expensive to use and oxygen has a great potential to explode, making it much more hazardous to handle. After limonene is oxidized and becomes a potent, stable bactericide, regardless of whether it is produced by the addition of air or oxygen, it retains its antimicrobial activity when stored, maintains its pleasant terpenic aroma (as opposed to the rancid odor of auto-oxidized limonene), and changes physical characteristics with an increased viscosity and an increased specific gravity. While the majority of limonene specimens which are purposely oxidized develop a potent, rapidly bactericidal activity, occasional limonene specimens do not become bactericidal with oxidation regardless of the length of, or the method of, oxidation. Thus, every batch of limonene which is purposely oxidized (to produce RBE limonene) must be individually tested for bactericidal activity. In short, the applicant's preferred method of producing oxidized limonene with a potent, stable bactericidal activity is to bubble air into limonene, because bubbling air through limonene is less expensive than using oxygen, and is less hazardous to use than oxygen.

Oxidized limonene is slightly viscous and readily adheres to glass, metal, wood, cloth, rope, book covers, cement, canvas, ceramic tile, plant surfaces, skin, mucous membranes and teeth leaving a film of oil. In practice, any surface on which it is desirable to kill or prevent bacterial or fungal growth, is contacted directly with bactericidal or fungicidal concentrations of limonene which has been oxidized until it has developed a minimum bactericidal concentration of at least 0.06 or less for Staphylococcus aureus ATCC 25923 when incubated for sixty minutes. It can be applied by swabbing, wiping, painting, washing, brushing, spraying, or any other direct application technique. Alternatively, it can be incorporated in creams, ointments, tinctures, gels, suppositories, paints, sprays, aerosols, toothpastes, solutions, emulsions, surgical soaps, mouthwashes, or antiseptics and can be applied anywhere it is desirable to kill or prevent the growth of bacteria, fungi, or yeasts.

BEST MODE FOR CARRYING OUT THE INVENTION

The following examples are illustrative of the best mode for carrying out the invention. They are, obviously, not to be construed as limitative of the invention since various other embodiments can readily be evolved in view of the teachings provided herein.

EXAMPLE 1

In Example 1, the several methods of producing purposely oxidized limonene that is bactericidal are demonstrated. In the first example, the process of bubbling air into limonene to produce oxidized limonene that is bactericidal at a concentration of 0.06 or less for *Staphylococcus aureus* ATCC 25923 when incubated for 60 minutes is shown in Table A below. The method of producing auto-oxidized limonene is shown in Table B.

The process of producing purposely oxidized limonene and auto-oxidized limonene was as follows: Four gallons of fresh d-limonene (Florida Chemical Company, Inc., Lake Alfred, Florida) were divided into one gallon portions in small-mouthed metal container. Two portions were treated at room temperature (~25° C.) while two were treated at 50° C. (in a water bath). For each temperature, one portion was left open to room air (auto-oxidized) while the second portion was actively oxidized by continuously bubbling air through it with a Second Nature Challenger I Pump aerator (purposely oxidized). Aliquots were removed from each of the four portions at 0, 2, 4, 6, 8, 10, 12, 14, and 16 weeks. For each aliquot, the viscosity, specific gravity, peroxide value and the antibacterial activity against *Staphylococcus aureus* ATCC 25923 and *Escherichia coli* ATCC 25922 were determined as outlined in Tables A, B, D, and E below.

For those portions treated at room temperature (Tables A and B), there was a clear difference in the type and potency of the antibacterial activity produced through the purposeful oxidation and auto-oxidation of d-limonene. The purposely oxidized limonene (Table A) showed maximum bactericidal activity by 6 to 8 weeks of treatment. It was rapidly bactericidal (10 minutes exposure) at dilutions up to 1:6.25 for *S. aureus* ATCC 25923 and 1:800 for *E. coli* ATCC 25922. It was bactericidal at dilutions of 1:1600 for both organisms with more prolonged exposure time (24 hours).

TABLE A

Changes in Physical Parameters, Peroxide Value, and Bactericidal Activity of d-Limonene[1] During The Purposeful Oxidation of the Oil at Room Temperature.

| Purposeful Oxidation[2] at Room Temperature in Weeks | Bactericidal Concentration[3] For | | | | | | Peroxide Value[4] | Specific Gravity[5] | Kinematic Viscosity[6] |
|---|---|---|---|---|---|---|---|---|---|
| | S. aureus ATCC 25923 After Incubation for | | | E. coli ATCC 25922 After Incubation for | | | | | |
| | 10 Min. | 60 Min. | 24 Hr. | 10 Min. | 60 Min. | 24 Hr. | | | |
| 0(fresh) | >1[7] | >1 | 0.2 | 1 | 1 | 0.10 | 50.2 | 0.8439 | 1.035 |
| 2 | 1 | 0.5 | 0.0025 | 0.24 | 0.02 | 0.0012 | 344.3 | 0.8535 | 1.176 |
| 4 | 1 | 0.10 | 0.0006 | 0.06 | 0.0012 | 0.0006 | 327.2 | 0.9118 | 2.847 |
| 6 | 0.16 | 0.06 | 0.0012 | 0.0025 | 0.0012 | 0.0006 | 353.5 | 0.9679 | 10.910 |
| 8 | 0.24 | 0.06 | 0.0006 | 0.0012 | 0.0006 | 0.0003 | 334.2 | 1.0122 | 51.85 |
| 10 | 1 | 0.10 | 0.0012 | 0.10 | 0.0025 | 0.0012 | 405.8 | 1.0420 | 199.7 |
| 12 | 0.4 | 0.10 | 0.0025 | 0.005 | 0.0025 | 0.0006 | 389.8 | 1.0633 | 500.4 |
| 14 | 0.4 | 0.10 | 0.0025 | 0.06 | 0.010 | 0.0012 | 848.3 | 1.0665 | 1,268.00 |
| 16 | 0.4 | 0.16 | 0.0025 | 0.10 | 0.005 | 0.0006 | 929.9 | 1.0784 | 2,562.00 |

[1]Florida Chemical Co., Inc., Lake Alfred, Florida
[2]Air was bubbled continuously into 1 gallon of oil in a small-mouthed metal container with an aerator (Second Nature Challenger I Pump).
[3]Bactericidal concentration shown as the highest dilution of limonene (i.e. lowest concentration) killing at least 99.99% of the original inoculum.
[4]Milliequivalents peroxide/kg sample
[5]at 25° C.
[6]at 25° C. cSt
[7]Undiluted oil was not bactericidal for 99.99% of the original inoculum.

In contrast, limonene that had been allowed to auto-oxidize at room temperature (Table B) showed maximum bactericidal activity at 14 to 16 weeks of treatment, but never reached the potency of the purposely oxidized oil. Rapid bactericidal activity (at 10 minutes) against *S. aureus* ATCC 25923 was never seen with any dilution of the auto-oxidized oil and only weakly diluted oil (1:2.5–1:10) was rapidly bactericidal for *E. coli* ATCC 25922. Even with prolonged incubation (24 hours), the auto-oxidized oil's bactericidal potency was 17 times less than that of the purposely oxidized oil against *S. aureus* ATCC 25923 and four times less against *E. coli* ATCC 25922. Increasing the treatment time of the oil beyond 16 weeks resulted in an overall decrease in potency.

TABLE B

Changes in Physical Parameters, Peroxide Value, and Bactericidal Activity of d-Limonene[1] During Auto-Oxidation of the Oil at Room Temperature.

| Auto-Oxidation[2] at Room Temperature in Weeks | Bactericidal Concentration[3] For | | | | | | Peroxide Value[4] | Specific Gravity[5] | Kinematic Viscosity[6] |
|---|---|---|---|---|---|---|---|---|---|
| | S. aureus ATCC 25923 After Incubation for | | | E. coli ATCC 25922 After Incubation for | | | | | |
| | 10 Min. | 60 Min. | 24 Hr. | 10 Min. | 60 Min. | 24 Hr. | | | |
| 0(fresh) | >1[7] | >1 | 0.2 | 1 | 1 | 0.10 | 50.2 | 0.8439 | 1.035 |
| 2 | >1 | >1 | 0.01 | 1 | 0.24 | 0.005 | 163.5 | 0.8440 | 1.066 |
| 4 | >1 | >1 | 0.01 | 0.5 | 0.16 | 0.0025 | 199.5 | 0.8477 | 1.082 |
| 6 | >1 | >1 | 0.01 | 1 | 0.06 | 0.0025 | 229.5 | 0.8486 | 1.090 |
| 8 | 1 | 1 | 0.01 | 0.5 | 0.06 | 0.0012 | 288.2 | 0.8510 | 1.124 |
| 10 | >1 | 1 | 0.005 | 1 | 0.06 | 0.0012 | 336.9 | 0.8548 | 1.167 |
| 12 | 1 | 0.5 | 0.01 | 0.10 | 0.01 | 0.0025 | 325.7 | 0.8570 | 1.198 |
| 14 | 1 | 0.4 | 0.01 | 0.40 | 0.0025 | 0.0012 | 366.1 | 0.8587 | 1.247 |

TABLE B-continued

Changes in Physical Parameters, Peroxide Value, and Bactericidal Activity of d-Limonene[1]
During Auto-Oxidation of the Oil at Room Temperature.

| Auto-Oxidation[2] at Room Temperature in Weeks | Bactericidal Concentration[3] For | | | | | | Peroxide Value[4] | Specific Gravity[5] | Kinematic Viscosity[6] |
|---|---|---|---|---|---|---|---|---|---|
| | S. aureus ATCC 25923 After Incubation for | | | E. coli ATCC 25922 After Incubation for | | | | | |
| | 10 Min. | 60 Min. | 24 Hr. | 10 Min. | 60 Min. | 24 Hr. | | | |
| 16 | 1 | 0.4 | 0.01 | 0.10 | 0.01 | 0.0025 | 393.8 | 0.8626 | 1.299 |
| 21 | >1 | 1 | 0.005 | 0.16 | 0.005 | 0.0025 | | | |

[1]Florida Chemical Co., Inc., Lake Alfred, Florida
[2]1 gallon of oil in small-mouthed metal container left open to room air.
[3]Bactericidal concentration shown as the highest dilution of limonene (i.e. lowest concentration) killing at least 99.99% of the original inoculum.
[4]Milliequivalents peroxide/kg sample
[5]at 25° C.
[6]at 25° C. cSt
[7]Undiluted oil was not bactericidal for 99.99% of the original inoculum.

For the purposely oxidized limonene (Table A), neither the highest peroxide value nor kinematic viscosity corresponded to the greatest antibacterial potency. This suggested that the antibacterial activity was not due solely to peroxides formed during oxidation nor was it due to mere concentration of antibacterial substances resultant from the evaporation that occurred during treatment. For the auto-oxidized limonene, antibacterial activity followed the peroxide value and kinematic viscosity up to 16 weeks. This suggested that the antibacterial may have been due, in large part, to peroxides and concentration of antibacterial substances during treatment. A comparison of the antibacterial effects of the two oils when each had a similar peroxide value clearly reveals the distinct nature of the activity of the purposely oxidized limonene (Table C). The auto-oxidized oil was not bactericidal at any dilution for either test organism after short exposure (10 minutes) while the purposely oxidized oil was bactericidal at a dilution of 1:4.2 for S. aureus ATCC 25923 and 1:800 for E. coli ATCC 25922. Even with prolonged exposure (24 hours), the bactericidal potency of the auto-oxidized oil was four to eight times less than that of the purposely oxidized oil.

TABLE C

Comparison of the Antibacterial Effect of Purposely Oxidized d-Limonene and Auto-Oxidized d-Limonene.[1]

| d-Limonene Preparation | Peroxide Value | Bactericidal Concentration For | | | | | |
|---|---|---|---|---|---|---|---|
| | | S. aureus ATCC 25923 After Incubation For | | | E. coli ATCC 25922 After Incubation For | | |
| | | 10 Min. | 60 Min. | 24 Hr. | 10 Min. | 60 Min. | 24 Hr. |
| Purposely Oxidized, 8 Weeks | 334.2 | 0.24 | 0.06 | 0.0006 | 0.0012 | 0.0006 | 0.0003 |
| Auto-Oxidized, 10 Weeks | 336.9 | >1 | 1 | 0.005 | 1 | 0.06 | 0.0012 |

[1]Compiled from Tables A and B

Increasing the -temperature of oxidation from room temperature (~25° C.) to 50° C. did not uniformly decrease the time necessary to produce potent, antibacterial activity in the oils (Tables D and E). For the purposely oxidized limonene, maximum bacterial activity was reached after only 3 weeks oxidation (Table D). This was in contrast to the 6 to 8 weeks required for purposeful oxidation at room temperature (Table A). However, the rapid bacterial potency (10 minutes exposure) was 6 to 83 times less for oil purposely oxidized at 50° C. in comparison to that purposely oxidized at room temperature. Thus, the two processes appeared to be generating oils with unique antibacterial effects. The oil purposely oxidized at 50° C. became so viscous at 6 weeks, it could not be tested further for antibacterial activity since it would not mix with the broth diluent in the assay.

Auto-oxidation of limonene at 50° C. produced an oil with even more distinct antibacterial activity (Table E).

TABLE D

Changes in Physical Parameters, Peroxide Value, and Bactericidal Activity of d-Limonene[1]
During The Purposeful Oxidation of the Oil at 50° C..

| Purposeful Oxidation[2] at 50° C. in Weeks | Bactericidal Concentration[3] For | | | | | | Peroxide Value[4] | Specific Gravity[5] | Kinematic Viscosity[6] |
|---|---|---|---|---|---|---|---|---|---|
| | S. aureus ATCC 25923 After Incubation for | | | E. coli ATCC 25922 After Incubation for | | | | | |
| | 10 Min. | 60 Min. | 24 Hr. | 10 Min. | 60 Min. | 24 Hr. | | | |
| 0(fresh) | >1[7] | >1 | 0.2 | 1 | 1 | 0.1 | 50.2 | 0.8439 | 1.035 |
| 2 | 1 | 0.16 | 0.0012 | 0.1 | 0.0006 | 0.0006 | 286.1 | 0.9549 | 8.203 |
| 4 | 1 | 0.5 | 0.0012 | 0.1 | 0.0025 | 0.0006 | 273.2 | 1.0300 | 141.9 |
| 6[8] | 1 | 0.4 | 0.01 | 0.01 | 0.005 | 0.0025 | 307.9 | 1.0670 | 1293 |
| 8 | | | | | | | 226.2 | 1.0784 | 3149 |
| 10 | | | | | | | 241.9 | 1.0863 | 10,526 |

[1]Florida Chemical Co., Inc., Lake Alfred, Florida
[2]Air was bubbled continuously into 1 gallon of oil in a small-mouthed metal container with an aerator (Second Nature Challenger I Pump).
[3]Bactericidal concentration shown as the highest dilution of limonene (i.e. lowest concentration) killing at least 99.99% of the original inoculum.
[4]Milliequivalents peroxide/kg sample
[5]at 25° C.
[6]at 25° C. cSt
[7]Undiluted oil was not bactericidal for 99.99% of the original inoculum.
[8]Oil too viscous to permit testing for antibacterial activity after 6 weeks and for other parameters after 10 weeks.

Fourteen weeks of treatment were required to maximize its rapid bacterial effects (10 minutes exposure) while two to four weeks of treatment were required to maximize its longer interval (24 hours) killing. This was similar to the time interval required to maximize the rapid and longer interval bactericidal effects of limonene auto-oxidized at room temperature (Table B). However, for the limonene auto-oxidized at 50° C., the bactericidal activity determined after long interval exposure (24 hours) decreased after 4 weeks treatment when the test organism was S. aureus ATCC 25923 but not when it was E. coli ATCC 25922. These results indicated that auto-oxidation of limonene at 50° C. could not produce the same bacterial activity as purposeful oxidation of limonene at room temperature.

dation of limonene at room temperature. The substances in the oil responsible for the rapid bactericidal activity appear to be heat labile (since they were not generated at 50° C.) and are clearly not peroxides. Longer interval bactericidal effects can be produced in limonene by a variety of treatments, and these too appear unrelated to peroxide content of the oils. However, only purposeful oxidation of limonene at room temperature results in an oil with both rapid and longer interval bactericidal activity at low concentrations.

TABLE F

Maximal Bactericidal Activity and Peroxide Value of Various Limonene Preparations.[1]

| Limonene Preparation | Rapid[2] Bactericidal Activity Against | | | | Long-Interval[3] Bactericidal Activity Against | | | |
|---|---|---|---|---|---|---|---|---|
| | S. aureus ATCC 25923 | | E. coli ATCC 25922 | | S. aureus ATCC 25923 | | E. coli ATCC 25922 | |
| A. Maximal Bactericidal Activity[4] | | | | | | | | |
| Purposely Oxidized, Room Temperature | 0.16 | (6)[6] | 0.0025 | (6) | 0.0012 | (6) | 0.0006 | (6) |
| Purposely Oxidized, 50° C. | 1 | (2) | 0.1 | (2) | 0.0012 | (2) | 0.0006 | (2) |
| Auto-Oxidized, Room Temperature | 1 | (16) | 0.1 | (16) | 0.01 | (2) | 0.0025 | (4) |
| Auto-Oxidized, 50° C. | 1 | (14) | 0.01 | (14) | 0.0025 | (2) | 0.0012 | (2) |
| B. Peroxide Value[5] of Oils with Maximal Bactericidal Activity | | | | | | | | |
| Purposely Oxidized, Room Temperature | 353.5 | | 353.5 | | 353.5 | | 353.5 | |
| Purposely Oxidized, 50° C. | 286.1 | | 286.1 | | 286.1 | | 286.1 | |
| Auto-Oxidized, Room Temperature | 393.8 | | 393.8 | | 163.5 | | 199.5 | |
| Auto-Oxidized, 50° C. | 211.0 | | 211.0 | | 308.8 | | 308.8 | |

[1]Data from Tables A, B, D, and E
[2]Measured after 10 min. exposure of the test organism to the oil
[3]Measured after 24 hr. exposure of the test organism to the oil
[4]Shown as highest dilution of oil killing 99.99% of bacterial inoculum
[5]Milliequivalents peroxide/kg sample
[6]Number in parentheses indicates weeks of treatment of the oil.

The appearances of the oils following six weeks of the four treatment regimens are quite different. For purposely oxidized limonene, the oil treated at 50° C. was darker yellow and more viscous than that treated at room temperature. For auto-oxidized, the oil treated at

TABLE E

Changes in Physical Parameters, Peroxide Value, and Bactericidal Activity of d-Limonene[1] During Auto-Oxidation of the Oil at 50° C..

| Auto-Oxidation[2] at 50° C. in Weeks | Bactericidal Concentration[3] For | | | | | | Peroxide Value[4] | Specific Gravity[5] | Kinematic Viscosity[6] |
|---|---|---|---|---|---|---|---|---|---|
| | S. aureus ATCC 25923 After Incubation for | | | E. coli ATCC 25922 After Incubation for | | | | | |
| | 10 Min. | 60 Min. | 24 Hr. | 10 Min. | 60 Min. | 24 Hr. | | | |
| 0(fresh) | >1[7] | >1 | 0.2 | 1 | 1 | 0.1 | 50.2 | 0.8439 | 1.035 |
| 2 | >1 | 1 | 0.0025 | 0.5 | 0.02 | 0.0012 | 308.8 | 0.8743 | 1.559 |
| 4 | >1 | 1 | 0.0025 | 0.4 | 0.02 | 0.0012 | 268.0 | 0.8906 | 2.010 |
| 6 | >1 | 1 | 0.02 | 0.16 | 0.0025 | 0.0025 | 217.5 | 0.9005 | 2.406 |
| 8 | 1 | 1 | 0.01 | 0.2 | 0.0025 | 0.0012 | 189.6 | 0.9056 | 2.700 |
| 10 | 1 | 1 | 0.01 | 0.1 | 0.005 | 0.0012 | 182.5 | 0.9135 | 3.168 |
| 12 | >1 | 1 | 0.02 | 0.1 | 0.0025 | 0.0025 | 192.6 | 0.9201 | 3.748 |
| 14 | 1 | 0.5 | 0.02 | 0.01 | 0.0025 | 0.0025 | 211.0 | 0.9282 | 4.544 |
| 16 | 1 | 0.5 | 0.06 | 0.1 | 0.0025 | 0.0025 | 219.6 | 0.9363 | 5.516 |
| 21 | >1 | 1 | 0.02 | 0.06 | 0.005 | 0.005 | | | |

[1]Florida Chemical Co., Inc., Lake Alfred, Florida
[2]1 gallon of oil in small-mouthed metal container left open to room air.
[3]Bactericidal concentration shown as the highest dilution of limonene (i.e. lowest concentration) killing at least 99.99% of the original inoculum.
[4]Milliequivalents peroxide/kg sample
[5]at 25° C.
[6]at 25° C. cSt
[7]Undiluted oil was not bactericidal for 99.99% of the original inoculum.

A summary of the maximal bactericidal activity obtained following treatment of limonene by the four processes described in the previous paragraphs is given in Table F. This activity has been separated into rapid bactericidal effects (10 minutes exposure) and longer-interval bactericidal effects (24 hours exposure) to emphasize the unique nature of the activity produced by the purposeful oxidation of limonene at room temperature. From this summary it is clear that the rapid bacterial activity can be produced only with purposeful oxiroom temperature was essentially unchanged in its appearance from untreated (fresh) limonene. Limonene auto-oxidized at 50° C. was similar in appearance to that purposely oxidized at room temperature.

From the data presented in Tables A, B, D, and E, a single point was selected as a reference point to indicate that any future oxidized limonene was "fully oxidized". The reference bactericidal endpoint (RBE) selected was a bactericidal activity at a dilution of at least 1:16.7

(0.06) when tested against *S. aureus* ATCC 25923 for 60 minutes exposure. This end point was selected because it (a) was found to be highly reproducible and required a greater dilution of oil than any 10 minute exposure endpoint, and (b) was an indicator for the presence of a rapid bactericidal effect against *S. aureus* and *E. coli*, and (c) was not obtained with any of the treatments of d-limonene except purposeful oxidation at room temperature. Thus, hereafter, all oxidized limonene achieving this reference bacterial endpoint is referred to as RBE limonene.

The standard assay used to test the bactericidal activity against *Staphylococcus aureus* ATCC 25923 or *Escherichia coli* ATCC 25922 in Tables A, B, C, D, E, F, H, I, & J was as follows: various volumes of the desired limonene were added to Mueller-Hinton broth, mixed vigorously (Vortex Genie Mixer, Scientific Products, Evanston, Ill.), inoculated with $10^6$ colony forming units (CFU)/ml of *Staphylococcus aureus* ATCC 25923 or *Escherichia coli* ATCC 25922, remixed and incubated at 37° C. in air. In varying the volume of the desired limonene to broth, concentrations of 1 (undiluted) to 0.01 (1:100 dilution) could be tested in a final volume of one to five ml (Table G). Higher dilutions of limonene (up to 1:51,200) were tested by preparing serial two-fold dilutions from the 0.01 dilution (i.e. equal volumes of limonene-containing broth and broth were mixed serially). At various time intervals, each tube was mixed vigorously and a 0.01 aliquot removed and subcultured on 5% sheep blood agar plates to determine the approximate number of viable CFU/ml in each tube. Results of these assays were expressed as the highest dilution of limonene with no detectable viable colonies on subculture i.e. the bactericidal concentration. This represented the lowest concentration killing 99.99 percent of the original inoculum.

TABLE G

To ascertain if a more potent bactericide could be produced through auto-oxidation of d-limonene when the process occurred over a large surface area of the oil, the following experiment was performed: Five hundred milliliters of fresh d-limonene (Intercit Inc., Safety Harbor, Florida) was equally divided into 250 ml portions. One portion was placed into a 500 ml Erlenmeyer flask while the second portion was placed in a 500 ml beaker. The beaker was left open, exposed to air at room temperature (auto-oxidized), while the sample in the flask was purposely oxidized at room temperature by continuously bubbling air through it with a Second Nature Challenger I Pump aerator (purposely oxidized limonene). An aliquot of 5 ml was removed from each (beaker or flask) at one, two, and three weeks. The viscosity, specific gravity, peroxide value, and the antibacterial activity against *S. aureus* ATCC 5923 of each aliquot was determined as previously outlined. In this experiment, auto-oxidation could take place over a larger surface area of the oil than in the prior experiment (performed in the small-mouthed container). Purposeful oxidation was still performed in a small-mouthed container in this experiment to prevent any ancillary auto-oxidation.

As shown in Table H, auto-oxidation of d-limonene at room temperature over a large surface area of the oil, did not produce a highly bactericidal oil. The characteristics of the oil found at three weeks were most similar to those of limonene auto-oxidized over a small surface area after six weeks (Table B). However, oxidation over a large surface area could not be continued for prolonged periods because evaporation of the oil led to a product too viscous to examine for bactericidal activity. Thus, auto-oxidation of limonene over a large surface area did not product a rapidly bactericidal oil and evaporation precluded long-term oxidation under these conditions.

TABLE H

Changes in the physical parameters, peroxide value, and bactericidal activity of d-limonene[1] during auto-oxidation of the oil over a large surface area.

| Auto-oxidation at Room Temperature in Weeks | Bactericidal Concentration[2] After Incubation for | | | Peroxide[3] Value | Specific[4] Gravity | Viscosity[5] |
| --- | --- | --- | --- | --- | --- | --- |
| | 10 Min | 60 Min | 24 Hrs | | | |
| 0 (Fresh) | >1[6] | >1 | >1 | 68.7 | 0.8432 | 1.024 |
| 1 | >1 | >1 | >1 | 131.2 | 0.8438 | 1.036 |
| 2 | >1 | >1 | >1 | 170.5 | 0.8434 | 1.052 |
| 3 | >1 | >1 | 0.01 | 231.3 | 0.8454 | 1.071 |

[1]250 ml of fresh limonene (Intercit Inc., Safety Harbor, Fla. lot 509801) in an open beaker at room temperature
[2]Bactericidal concentration shown as the highest dilution (i.e. lowest concentration) killing at least 99.99% of the original inoculum of *S. aureus* ATCC 25923
[3]Millequiv. peroxide/kg sample
[4]at 25° C.
[5]cSt at 25° C.
[6]Undiluted oil was not bactericidal

| Dilutions of limonene used in fixed volume assays | |
| --- | --- |
| Dilutions Tested | Limonene Concentration |
| Undiluted | 1 |
| 1:2 | 0.5 |
| 1:2.5 | 0.4 |
| 1:3.3 | 0.3 |
| 1:4.2 | 0.24 |
| 1:5 | 0.2 |
| 1:6.25 | 0.16 |
| 1:10 | 0.1 |
| 1:6.25 | 0.06 |
| 1:50 | 0.02 |
| 1:100 | 0.01 |

The bactericidal activity of purposely oxidized limonene in this experiment is shown in Table I. As was seen before, a rapidly bactericidal oil was produced by this process. The source of the oil was completely different than that shown in Table A, and the reference endpoint (i.e. bactericidal at a concentration of 0.06 or less for *S. aureus* ATCC 25923) was reached sooner than the previous experiment. These results suggested that different lots of limonene may require different treatment times for purposeful oxidation to reach the defined reference endpoint.

TABLE I

Changes in the physical parameters, peroxide value, and bactericidal activity of d-limonene[1] during purposeful oxidation of the oil.

| Purposeful oxidation at Room Temperature in Weeks[2] | Bactericidal Concentration[3] After Incubation for | | | Peroxide[4] Value | Specific[5] Gravity | Viscosity[6] |
|---|---|---|---|---|---|---|
| | 10 Min | 60 Min | 24 Hrs | | | |
| 0 (Fresh) | >1[7] | >1 | >1 | 68.7 | 0.8432 | 1.024 |
| 1 | 0.1 | 0.1 | 0.1 | 131.2 | 0.8438 | 1.036 |
| 2 | 0.1 | 0.1 | 0.0025 | 170.5 | 0.8434 | 1.052 |
| 3 | 0.1 | 0.1 | 0.00125 | 231.3 | 0.8454 | 1.071 |

[1]Intercit Inc., Safety Harbor, Florida, lot 509801
[2]Air bubbled continuously into 250 ml of limonene in a 500 ml Erlenmeyer flask with an aerator (Second Nature Challenger I Pump) at room temperature.
[3]Bactericidal concentration shown as the highest dilution (i.e. lowest concentration) killing at least 99.99% of the original inoculum of *S. aureus* ATCC 25923.
[4]millequiv. peroxide/kg sample
[5]at 25° C.
[6]cSt at 25° C.
[7]Undiluted oil was not bactericidal The ability of purposeful oxidation of limonene to produce a rapidly bactericidal oil was determined using limonene from various sources. As shown in Table J, not all samples of limonene became bactericidal with purposeful oxidation at room temperature. Two samples from Aldrich did not acquire bactericidal activity even after purposeful oxidation for five weeks while one sample obtained from this same source became rapidly bactericidal in as short as three weeks. Also, as shown in Table J, both d- and l- isomers of limonene can be purposely oxidized to become a rapid bactericide. These data emphasize the need to test every batch of purposely oxidized limonene after three to eight weeks treatment to ensure that the reference bactericidal endpoint has been reached.

TABLE J

Antibacterial Activity Of Various Limonene Samples As Determined Against *Staphylococcus aureus* ATCC 25933 During Purposeful Oxidation at Room Temperature.

| Sample | Source | Duration of Purposeful Oxidation | Bactericidal Concentration After Incubation For | | |
|---|---|---|---|---|---|
| | | | 10 Mins | 60 Mins | 24 Hours |
| d-limonene | Aldrich[1] | 5 weeks | >1[5] | >1 | >1 |
| l-limonene | Aldrich[1] | 5 weeks | >1 | >1 | >1 |
| l-limonene | SCM[1] | 3 weeks | >1 | >1 | >1 |
| d-limonene | Intercit[3] | 3 weeks | 0.1 | 0.005 | 0.0003 |
| l-limonene | SCM[1] | 3 weeks | 0.1 | 0.005 | 0.0006 |
| d-limonene | Aldrich[1] | 3 weeks | 0.005 | 0.0024 | 0.0003 |
| d-limonene | FCC[1] | 6 weeks | 0.16 | 0.06 | 0.0012 |

[1]Aldrich, Milwaukee, Wisconsin
[2]SCM Glidden Organics, Jacksonville, Florida
[3]Intercit, Inc., Safety Harbor, Florida
[4]Florida Chemical Company, Inc., Lake Alfred, Florida
[5]Undiluted oil was not bactericidal The second method of producing RBE limonene is by continuously bubbling oxygen into limonene as outlined in Table K below. This process, like bubbling air through limonene produces a rapidly bactericidal oil and requires 6 to 7 weeks treatment for the reference endpoint to be achieved.

TABLE K

Bactericidal Activity of d-limonene[1] During Oxygenation As Determined Against *Staphylococcus aureus* ATCC 25923

| Days d-Limonene Oxidized[3] at 25° C. | Bactericidal Concentration[2] Following Incubation For: | | |
|---|---|---|---|
| | 15 Min | 60 Min | 24 Hours |
| 0 days | >1[4] | >1 | >1 |
| 1 day | >1 | >1 | 0.01 |
| 2 days | >1 | >1 | 0.01 |
| 3 days | >1 | >1 | 0.01 |
| 4 days | >1 | >1 | 0.01 |
| 7 days | >1 | >1 | 0.005 |
| 9 days | >1 | >1 | 0.005 |
| 15 days | 0.5 | 0.5 | 0.005 |
| 17 days | 0.5 | 0.5 | 0.001 |
| 24 days | >1 | 0.16 | 0.005 |
| 36 days | 0.5 | 0.10 | 0.0006 |
| 45 days | 0.16 | 0.06 | 0.001 |
| 49 days | 0.16 | 0.06 | 0.003 |
| 53 days | 0.3 | 0.06 | 0.003 |
| 59 days | 0.10 | 0.02 | 0.003 |
| 66 days | 0.16 | 0.01 | 0.003 |
| 73 days | 0.01 | 0.01 | 0.003 |

[1]Fresh d-limonene (Intercit Inc., Safety Harbor, Florida lot 509801)
[2]Results expressed as the highest dilution of limonene killing at least 99.99% of the original inoculum.
[3]Oxygen bubbled continuously into d-limonene at a rate of 3 liter per min at 25° C..
[4]Undiluted oil was not bactericidal.

EXAMPLE 2

In Example 2 the bactericidal and fungicidal activity of RBE d-limonene and RBE l-limonene was determined against bacteria, yeasts, and fungi as outlined in Tables L & M below.

TABLE L

BACTERICIDAL AND FUNGICIDAL ACTIVITY OF RBE d-LIMONENE

| ORGANISM | BACTERICIDAL CONCENTRATION AFTER INCUBATION FOR | | |
|---|---|---|---|
| | 10 Min | 60 Min | 24 Hours |
| A. BACTERIA | | | |
| 1. *Staphylococcus aureus*, ATCC 25923 | 0.3 | 0.06 | 0.0012 |
| 2. *Staphylococcus aureus* 3* | 1.00 | 0.10 | 0.001 |
| 3. *Staphylococcus aureus* 27** | 1.00 | 0.10 | 0.001 |
| 4. *Staphylococcus aureus* 37* | 0.30 | 0.06 | 0.0025 |
| 5. *Staphylococcus aureus* 39** | 0.30 | 0.06 | 0.0015 |
| 6. *Staphylococcus aureus* 52T | 0.30 | 0.06 | 0.0012 |
| 7. *Staphylococcus aureus* 53T | 0.30 | 0.06 | 0.0025 |

TABLE L-continued
BACTERICIDAL AND FUNGICIDAL ACTIVITY OF RBE d-LIMONENE

| ORGANISM | | | |
|---|---|---|---|
| 8. Staphylococcus aureus 54T | 0.30 | 0.06 | 0.0025 |
| 9. Staphylococcus epidermidis 10 | 1.00 | 0.10 | 0.001 |
| 10. Sarcinia lutea | 1.00 | 0.01 | 0.001 |
| 11. Streptococcus mitis 15 (alpha) | 0.01 | 0.01 | 0.001 |
| 12. Streptococcus pyogenes 1 (group A) | 0.01 | 0.01 | 0.01 |
| 13. Streptococcus salivarius (gamma) | 0.01 | 0.01 | 0.01 |
| 14. Streptococcus mutans | 0.16 | 0.06 | 0.0012 |
| 15. Streptococcus faecalis 15 | 1.00 | 0.10 | 0.01 |
| 16. Lactobacillus casei M7 | 0.01 | 0.01 | 0.01 |
| 17. Listeria monocytogenes M9 | 0.01 | 0.01 | 0.01 |
| 18. Bacillus subtilis ATCC 6633 | 0.01 | 0.001 | 0.001 |
| 19. Escherichia coli 7 | 0.01 | 0.01 | 0.01 |
| 20. Klebsiella SP12 | 0.01 | 0.01 | 0.001 |
| 21. Salmonella 14 (para B) | 0.01 | 0.01 | 0.01 |
| 22. Shigella sonnei 8 | 0.01 | 0.001 | 0.001 |
| 23. Proteus mirabilis 2 | 0.01 | 0.01 | 0.01 |
| 24. Proteus vulgaris 127 | 0.10 | 0.01 | 0.01 |
| 25. Proteus rettgeri 106 | 0.10 | 0.01 | 0.10 |
| 26. Proteus morganii 99 | 0.01 | 0.01 | 0.01 |
| 27. Providencia stuartii 97 | 0.01 | 0.01 | 0.01 |
| 28. Enterobacter cloacae 20 | 0.01 | 0.01 | 0.10 |
| 29. Citrobacter SP8 | 0.01 | 0.01 | 0.10 |
| 30. Pseudomonas aeruginosa 115 | 0.10 | 0.10 | 0.01 |
| 31. Pseudomonas mendocina 129 | 1.0 | 0.10 | 0.01 |
| 32. Neisseria gonorrhea 5 | 0.001 | 0.001 | 0.001 |
| 33. Neisseria gonorrhea (Pen R)* | 0.001 | 0.001 | 0.001 |
| 34. Hemophilus influenzae (Amp R)** | 0.01 | 0.001 | 0.001 |
| 35. Hemophilus influenzae (Amp S)*** | 0.0001 | 0.001 | 0.001 |
| 36. Neisseria meningitidis | 0.001 | 0.001 | 0.001 |
| 37. Xanthomonas campestris PV vesicatoria 1 | 0.0012 | 0.0003 | 0.0003 |
| 38. Xanthomonas campestris PV vesicatoria 2 | 0.0012 | 0.0003 | 0.0003 |
| 39. Xanthomonas (SP) *+ isolated from a Nebraska farmer | 0.0025 | 0.0003 | 0.0003 |
| 40. Xanthomonas campestris PV citri | 0.005 | 0.0025 | 0.0006 |
| 41. Mycobacterium tuberculosis var hominis H37 RV | 0.001 | 0.001 | 0.0001 |
| 42. Mycobacterium kansasii Tam 30 | 0.1 | 0.01 | 0.0001 |
| 43. Mycobacterium scrofulaceum | 0.1 | 0.01 | 0.0001 |
| 44. Mycobacterium intracellulare | 0.1 | 0.10 | 0.0001 |
| 45. Mycobacterium fortuitum ATCC 6841 | 1.0 | 0.10 | 0.0001 |
| B. YEASTS | | | |
| 1. Candida albicans | 0.01 | 0.001 | 0.001 |
| 2. Sacchromyces SP | 0.01 | 0.01 | 0.001 |

| | FUNGICIDAL CONCENTRATION AFTER INCUBATION FOR | | | |
|---|---|---|---|---|
| | 10 Min | 60 Min | 24 Hours | 7–45 Days |
| C. FUNGI | | | | |
| 1. Epidermophyton floccosum | | | | 0.001 |
| 2. Microsporum audouini | | | | 0.001 |
| 3. Microsporum canis | 0.01 | 0.0025 | 0.0006 | |
| 4. Trichophyton mentagrophytes | | | | 0.001 |
| 5. Aureoblasidium pullulans OM 279C | 0.01 | 0.005 | 0.0012 | |
| 6. Cladosporium cladosporiodes OM 489 | 0.01 | 0.005 | 0.0012 | |
| 7. Philopohora lignicola OM 5922 | 0.10 | 0.01 | 0.0025 | |

*Penicillin resistant
**Ampicillin resistant
***Ampicillin sensitive
*+Species unidentified

TABLE M
BACTERICIDAL AND FUNGICIDAL ACTIVITY OF RBE l-LIMONENE

| ORGANISM | BACTERICIDAL CONCENTRATION AFTER INCUBATION FOR | | |
|---|---|---|---|
| | 10 Min | 60 Min | 24 Hours |
| A. BACTERIA | | | |

TABLE M-continued
BACTERICIDAL AND FUNGICIDAL ACTIVITY OF RBE l-LIMONENE

| ORGANISM | | | |
|---|---|---|---|
| 1. Staphylococcus aureus ATCC 25923 | 0.5 | 0.06 | 0.0025 |
| 2. Staphylococcus aureus 37 (Pen R)* | 0.5 | 0.40 | 0.005 |
| 3. Staphylococcus aureus 39 (Meth R)** | 0.3 | 0.06 | 0.0025 |
| 4. Staphylococcus aureus 52T | 0.5 | 0.10 | 0.01 |
| 5. Staphylococcus aureus 53T | 0.5 | 0.10 | 0.0025 |
| 6. Staphylococcus aureus 54T | 0.5 | 0.06 | 0.01 |
| 7. Staphylococcus epidermidis 10 | 0.1 | 0.1 | 0.0025 |
| 8. Streptococcus mutans M42 | 0.3 | 0.16 | 0.005 |
| 9. Streptococcus faecalis 15 | 0.1 | 0.01 | 0.0025 |
| 10. Bacillus subtilis ATCC 6633 | 0.1 | 0.1 | 0.1 |
| 11. Escherichia coli 7 | 0.005 | 0.0025 | 0.0012 |
| 12. Salmonella 14 (Para B) | 0.0025 | 0.0025 | 0.0006 |
| 13. Shigella sonnei 8 | 0.01 | 0.0025 | 0.0012 |
| 14. Pseudomonas aeruginosa 115 | 0.1 | 0.1 | 0.005 |
| 15. Neisseria meningitidis 40 | 0.0012 | 0.0006 | 0.00004 |
| 16. Xanthomonas campestris vesicatoria 1 | 0.0025 | 0.0012 | 0.0012 |
| 17. Xanthomonas campestris vesicatoria 2 | 0.0025 | 0.0012 | 0.0003 |
| 18. Xanthomonas SP isolated from a Nebraska farmer*+ | 0.0006 | 0.0006 | 0.0003 |
| 19. Xanthomonas campestris PV citri | 0.005 | 0.0025 | 0.0006 |
| 20. Mycobacterium tuberculosis var hominis H37 RV | 0.0005 | 0.000125 | 0.000125 |
| 21. Mycobacterium fortuitum ATCC 6841 | 0.1 | 0.1 | 0.0006 |
| B. YEASTS | | | |
| 1. Candida albicans | 0.0012 | 0.0012 | 0.0006 |

| | FUNGICIDAL CONCENTRATION AFTER INCUBATION FOR | | |
|---|---|---|---|
| | 10 Min | 60 Min. | 24 Hours |
| C. FUNGI | | | |
| 1. Microsporum canis | 0.1 | 0.0025 | 0.0006 |
| 2. Aureoblasidium pullulans OM 279C | 0.01 | 0.005 | 0.0012 |
| 3. Cladosporium cladosporiodes OM 489 | 0.1 | 0.005 | 0.0012 |
| 4. Philopohora lignicola OM 5922 | 0.10 | 0.01 | 0.005 |

*Penicillin resistant
**Methicillin resistant
*+Unidentified species

The standard assay used to test the bactericidal activity of the d and l isomers of limonene which had been oxidized until they reached the reference bactericidal endpoint was as follows: various dilutions of the desired limonene were separately prepared in an appropriate broth medium for the test strain. An inoculum of $10^6$ colony-forming units (CFU)/ml was used. Each test was incubated at the proper temperature for each organism and subcultured (0.01 ml) at 10 minutes, 60 minutes and 24 hours onto agar media free of limonene.

Results were expressed as the bactericidal concentration, i.e., the lowest concentration of RBE limonene (ml limonene/total ml of test) killing at least 99.99% of the bacterial inoculum.

The activity of RBE limonene was evaluated against Mycobacteria using undiluted oil, and oil diluted up to 1:8000 in Proskauer Beck liquid medium. Each test was inoculated with $10^6$ CFU/ml of Mycobacteria and incubated at 37 degrees C. in 7% $CO_2$ in air. At various time intervals, each test was shaken vigorously and a 0.01 ml aliquot removed. This was subcultured onto Dubos oleic acid-albumin agar plates to determine the number of viable Mvcobacteria remaining. Each test was sampled in this fashion after incubation for 10 minutes, 60 minutes, 24 hours, 1, 2, 3, and 4 weeks. The bacterial concentration was defined as the lowest concentration of oil killing at least 99.99% of the original inoculum.

The standard assay used to test certain fungi (dermatophytes) was as follows: RBE d-limonene and RBE l-limonene were tested in air on sabouraud dextrose agar slants supplemented with 0.05% yeast extract. Each of the two compounds was individually added to different samples of molten agar in dilutions of 1:10, 1:15, 1:100, 1:1000 and then mixed vigorously after which the agar was allowed to solidify. The inoculum was prepared as follows: 10 ml of saline (0.85%) and four drops of tween 80 were added to sabouraud dextrose agar slants containing the fungus grown for 14 days at room temperature. After vigorous shaking, the culture was filtered through sterile gauze and adjusted to the density of a MacFarland Standard No. 1 with 0.85% saline. The limonene containing slants were inoculated with 0.1 ml of this adjusted suspension, incubated at room temperature and checked for growth daily for 43 days. After 7 days, confluent growth of each fungus was observed on limonene-free control slants. The fungicidal concentration of RBE limonene was defined as the lowest concentration preventing growth on the slants for 43 days.

The test conditions used to assay the antimicrobial activity of RBE limonene are listed in Table N which follows.

TABLE N

| ORGANISM | BROTH MEDIUM | SUBCULTURE AGAR MEDIUM | INCUBATION CONDITIONS |
|---|---|---|---|
| 1. Staphylococcus, Sarcina, Bacillus, Enterobacteriacea and Pseudomonas | Mueller-Hinton | 5% sheep blood | air @ 37° C. |
| 2. Streptococcus, Lactobacillus, Listeria | Todd-Hewitt | 5% sheep blood | 10% $CO_2$ in air @ 37° C. |
| 3. Neisseria meningitidis | Mueller-Hinton | 5% sheep blood | 10% $CO_2$ in air @ 37° C. |
| 4. Neisseria gonorrhea | Eugon | chocolate | 10% $CO_2$ in air @ 37° C. |
| 5. Hemophilus influenza | Levinthal | chocolate | 10% $CO_2$ in air @ 37° C. |
| 6. Yeast | Sabouraud dextrose | 5% sheep blood | air @ 37° C. |
| 7. Xanthomonas campestris vesicatoria & citri | Nutrient | blood agar | air @ 25° C. |
| 8. Xanthomonas species isolated from Nebraska farmer (species not identified) | Mueller-Hinton | blood agar | air @ 37° C. |
| 9. Mycobacteria | Proskauer Beck | Dubos-oleic acid-albumin agar | 7% $CO_2$ @ 37° C. |
| 10. Fungi | Sabourauds dextrose with 0.05% yeast extract | | |

In example 3, formulations, containing RBE limonene are listed.

RBE d-limonene and RBE l-limonene are prepared in the following formulations including liquids, gels, soaps, paints, pastes, creams, ointments, suppositories, tampons, aerosols, and emulsion. When bacteria, fungi or yeasts are treated with formulations that contain RBE d-limonene or RBE l-limonene, the formulations kill or prevent the growth of bacteria, yeasts, and fungi.

| CHEMICAL | % OF TOTAL | RANGE | ACTION |
|---|---|---|---|
| A. LIQUIDS | | | |
| 1. SOLUTIONS OR SPRAYS | | | |
| a. RBE d-Limonene | 6.0% | 0.1-50% | bactericide |
| Corn Oil | 94.0% | 50-99.9% | diluent |
| | 100.0% | | |
| b. RBE l-Limonene | 1.0% | 0.1-50% | fungicide |
| Ethyl Alcohol | 99.0% | 50-99.9% | diluent |
| | 100.0% | | |
| 2. MOUTHWASH | | | |
| a. RBE d-limonene | 50.0% | 0.1-50% | antiyeast |
| Flavor | 2.0% | 1-5% | flavor |
| Ethyl Alcohol | 48.0% | 45-98.9% | diluent |
| | 100.0% | | |
| B. DENTIFRICE | | | |
| 1. LIQUID | | | |
| Liquid soap concentrate | 5.0% | 2-10% | surfactant |
| Saccharin | 0.2% | 0.1-1.0% | flavor |
| Clove Oil | 1.0% | 0.5-3.0% | flavor |
| Cinnamon Oil | 0.5% | 0.5-3.0% | flavor |
| Peppermint Oil | 0.5% | 0.5-3.0% | flavor |
| Ethyl Alcohol | 42.6% | 29.5-95.3% | diluent |
| Color | 0.2% | 0.1-0.5% | color |
| RBE l-limonene | 50.0% | 1-50% | fungicide |
| | 100.0% | | |
| 2. GEL | | | |
| Sodium monofluorophosphate | 0.8% | 0.5-1.5% | antiplaque |
| RBE d-limonene | 50.0% | 1-50% | antibacterial |
| Hydrated silica xerogel | 10.0% | 8-15% | abrasive |
| Hydrated thickening silica | 8.5% | 5-10% | binder |
| Sorbitol 70% solution | 18.8% | 5-73.3% | humectant |
| Polyethylene glycol 32 | 5.0% | 3-7% | bodying agent |
| Sodium lauryl sulfate | 1.5% | 1-2% | surfactant |
| Carboxymethyl cellulose gum | 1.0% | 0.5-2% | binder |
| S D alcohol | 1.0% | 0.5-2% | stabilizer |
| Flavor | 3.0% | 2-4% | flavor |
| Saccharin | 0.2% | 0.1-0.5% | flavor |
| F D & C Green #3 | 0.1% | 0.1-0.5% | color |

-continued

| | CHEMICAL | % OF TOTAL | RANGE | ACTION |
|---|---|---|---|---|
| | F D & C Green #10 | 0.1% | 0.1–0.5% | color |
| | | 100.0% | | |
| 3. | PASTE | | | |
| | Sodium monofluorophosphate | 0.8% | 0.5–1.5% | antiplaque |
| | RBE l-limonene | 50.0% | 1–50% | fungicide |
| | Dicalcium phosphate dihydrate | 22.0% | 20.4–30% | abrasive |
| | Water | 16.0% | 11.1–69.5% | diluent |
| | Glycerine | 5.1% | 4.5–12.5% | bodying agent |
| | Flavor | 2.0% | 2–3% | flavor |
| | Sodium lauryl sulfate | 1.5% | 1–2% | surfactant |
| | Carboxymethyl cellulose gum | 1.4% | 0.5–2.0% | binder |
| | Tetrasodium pyrophosphate | 1.0% | 0.5–2.0% | binder |
| | Sodium saccharin | 0.2% | 0.1–0.5% | flavor |
| | | 100.0% | | |

C. OINTMENTS & SUPPOSITORIES WITH AND WITHOUT HYDROCORTISONE

| | | | % OF TOTAL | RANGE | ACTION |
|---|---|---|---|---|---|
| 1. | OINTMENT WITH HYDROCORTISONE | | | | |
| | RBE d-limonene | | 1.0% | 0.1–15.0% | bactericide |
| | Polyethylene glycol 3350 | | 59.0% | 48.5–59.7% | bodying agent & emulsifier |
| | Polyethylene glycol 400 | | 39.0% | 31.5–39.7% | bodying agent & emulsifier |
| | Hydrocortisone | | 1.0% | 0.5–5.0% | anti-inflammatory |
| | | | 100.0% | | |
| 2. | OINTMENT WITHOUT HYDROCORTISONE | | | | |
| | RBE l-limonene | | 1.0% | 0.1–15.0% | fungicide |
| | Polyethylene glycol 3350 | | 59.5% | 51.0–59.95% | bodying agent & emulsifier |
| | Polyethylene glycol 400 | | 39.5% | 34.0–39.95% | bodying agent & emulsifier |
| | | | 100.0% | | |
| 3. | SUPPOSITORY WITHOUT HYDROCORTISONE | | | | |
| | RBE l-limonene | | 6.0% | 0.1–15% | bactericide |
| | Polyethylene glycol 1000 | | 56.5% | 51.0–59.95% | bodying agent & emulsifier |
| | Polyethylene glycol 3350 | | 37.5% | 34.0–39.95% | bodying agent & emulsifier |
| | | | 100.0% | | |
| 4. | SUPPOSITORY WITH HYDROCORTISONE | | | | |
| | RBE d-limonene | | 1.0% | 0.1–15% | antiyeast |
| | Polyethylene glycol 1000 | | 74.0% | 60.0–75.2% | bodying agent & emulsifier |
| | Polyethylene glycol 3350 | | 24.0% | 20.0–24.2% | bodying agent & emulsifier |
| | Hydrocortisone | | 1.0% | 0.5–5.0% | anti-inflammatory |
| | | | 100.0% | | |

D. CREAMS WITHOUT HYDROCORTISONE

| | | % OF TOTAL | RANGE | ACTION |
|---|---|---|---|---|
| 1. | RBE l-limonene | 6.0% | 0.1–15.0% | bactericide |
| | Cetyl alcohol | 15.0% | 12.0–18.0% | thickener |
| | Arlacel 165** | 5.0% | 3.5–7.5% | emulsifier |
| | Sorbitol 70% solution | 5.0% | 3.5–8.0% | humectant |
| | Water | 69.0% | 51.5–80.9% | diluent |
| | | 100.0% | | |
| 2. | RBE l-limonene | 1.0% | 0.1–15.0% | fungicide |
| | Spermaceti wax | 12.5% | 10.0–15.0% | thickener |
| | Sorbitan monostearate* | 10.0% | 7.5–12.5% | emulsifier |
| | Sorbitol monostearate* Polyethylene 20 | 6.0% | 4.0–8.0% | emulsifier |
| | Water | 70.5% | 49.5–78.4% | diluent |
| | | 100.0% | | |

E. CREAMS WITH HYDROCORTISONE

| | | % OF TOTAL | RANGE | ACTION |
|---|---|---|---|---|
| 1. | RBE d-limonene | 1.0% | 0.1–15.0% | fungicide |
| | Cetyl alcohol | 15.0% | 12.0–18.0% | thickener |
| | Arlacel 165** | 5.0% | 3.5–7.5% | emulsifier |
| | Sorbitol 70% solution | 5.0% | 3.5–8.0% | humectant |
| | Hydrocortisone | 1.0% | 0.5–5.0% | anti-inflammatory |
| | Water | 73.0% | 46.5–80.4% | diluent |
| | | 100.0% | | |

F. TAMPONS

| | | % OF TOTAL | RANGE | ACTION |
|---|---|---|---|---|
| 1. | RBE d-limonene 2 cc 2 Gm | 8% | 1–15% | bactericide |
| | Tampon 23 Gm | 92% | 85–99% | reservoir for fungicide |
| | | 100% | | |

G. AEROSOLS WITHOUT HYDROCORTISONE

| | | % OF TOTAL | RANGE | ACTION |
|---|---|---|---|---|
| 1. | RBE l-limonene | 6.0% | 0.5–50% | bactericide |
| | Ethyl alcohol | 94.0% | 50–99.5% | diluent |

-continued

| | CHEMICAL | % OF TOTAL | RANGE | ACTION |
|---|---|---|---|---|
| | | 100.0% | | |
| | Pressurized nitrogen propellant at 100–125 psig | | | |
| 2. | RBE d-limonene | 10.0% | 0.5–50.0% | fungicide |
| | Soybean Oil | 90.0% | 50.0–99.5% | diluent |
| | | 100.0% | | |
| | Pressurized nitrogen propellant at 100–125 psig | | | |

H. AEROSOL WITH HYDROCORTISONE

| | CHEMICAL | % OF TOTAL | RANGE | ACTION |
|---|---|---|---|---|
| 1. | RBE l-limonene | 6.0% | 0.5–50% | bactericide |
| | Soybean oil | 93.0% | 45–99.0% | diluent |
| | Hydrocortisone | 1.0% | 0.5–5.0% | anti-inflammatory |
| | | 100.0% | | |
| | Pressurized nitrogen propellant at 100–125 psig | | | |

I. OIL IN WATER EMULSION

| | CHEMICAL | % OF TOTAL | RANGE | ACTION |
|---|---|---|---|---|
| 1. | RBE d-limonene | 0.1% | 0.1–50% | fungicide |
| 2. | Corn oil | 10.0% | 10–15% | oil |
| | Arlacel 40** | 2.0% | 1–3% | emulsifier |
| | Tween 40 | 3.0% | 2–4% | emulsifier |
| 3. | Water | 84.9% | 28–86.9% | diluent |
| | | 100.0% | | |

Heat 2 to 70° C.. Heat 3 to 72° C.. Add 3 to 2 with continuous agitation. When 3 and 2 cool to 40° C., add 1 with continuous agitation until room temperature is reached.

J. OIL IN WATER EMULSION WITH SOAP (FUNGICIDAL SOAP)

| | CHEMICAL | % OF TOTAL | RANGE | ACTION |
|---|---|---|---|---|
| 1. | RBE d-limonene | 10.0% | 0.1–25% | bactericide |
| 2. | Corn oil | 21.0% | 20.0–40.0% | oil |
| | Arlacel 40** | 2.0% | 1.0–3.0% | emulsifier |
| | Tween 40 | 3.0% | 2.0–4.0% | emulsifier |
| | Liquid soap concentrate | 3.5% | 2.5–5.0% | surfactant |
| 3. | Water | 60.5% | 23–74.4% | diluent |
| | | 100.0% | | |

Heat 2 to 70° C.. Heat 3 to 72° C.. Add 3 to 2 with continuous agitation. When 3 and 2 cool to 40° C., add 1 with continuous agitation until room temperature is reached.

K. WATER IN OIL EMULSION

| | CHEMICAL | % OF TOTAL | RANGE | ACTION |
|---|---|---|---|---|
| 1. | RBE l-limonene | 1.0% | 0.1–25% | fungicide |
| 2. | Arlacel 186** | 3.0% | 2.0–4.0% | emulsifier |
| | Soybean oil | 15.0% | 10.0–25.0% | oil |
| | Ceresin wax | 0.5% | 0.3–0.6% | thickener |
| | Beeswax | 0.5% | 0.3–0.6% | thickener |
| | Tween 40 | 0.5% | 0.3–0.6% | emulsifier |
| 3. | Water | 79.5% | 44.2–87.0% | diluent |
| | | 100.0% | | |

Heat 2 to 70° C.. Heat 3 to 72° C.. Add 3 to 2 with continuous agitation. When 3 and 2 cool to 40° C., add 1 with continuous agitation until room temperature is reached.

L. PAINT

1. ENAMEL

| CHEMICAL | % OF TOTAL | RANGE | ACTION |
|---|---|---|---|
| RBE l-limonene | 1.00% | 1–10% | fungicide |
| Titanium dioxide | 14.91% | 12–16% | pigment |
| Calcium carbonate | 29.83% | 25–35% | pigment |
| Silicate | 4.81% | 3–6% | pigment |
| Soya alkyd resin | 25.72% | 22–28% | pigment (binder) |
| Mineral spirits | 23.73% | 5–37% | solvent (thinner) |
| | 100.00% | | |

2. LATEX

| CHEMICAL | % OF TOTAL | RANGE | ACTION |
|---|---|---|---|
| RBE l-limonene | 1.00% | 1–10% | fungicide |
| Titanium dioxide | 10.76% | 8–12% | pigment |
| Silicate | 12.91% | 10–16% | pigment |
| Calcium carbonate | 20.91% | 15–25% | pigment |
| Vinyl acrylic resin solids | 12.22% | 10–16% | vehicle (binder) |
| Glycol | 8.30% | 6–10% | solvent (thinner) |
| Water | 34.00% | 12–50% | solvent (thinner) |
| | 100.00% | | |

*Croda, Inc., 51 Madison Ave., New York, New York 10010
**Glycerol monstearate and polyoxyethylene stearate ICI of America (Formerly Atlas Chemcial Industries), Wilmington, Delaware 19899

While only certain preferred embodiments of this invention have been shown and described by way of illustration, many modifications will occur to those skilled in the art and it is, therefore, desired that it be understood that it is intended herein, to cover all such modifications that fall within the true spirit and scope of this invention.

We claim:

1. A process for producing a stable, bactericidal and fungicidal composition that is bactericidal and fungicidal in bactericidal and fungicidal concentrations, which process consists essentially of bubbling air into limonene, or bubbling oxygen into limonene to produce an oxidized limonene having a rapid bactericidal activity as evidenced by the capability of killing at least 99.99% of the bacteria in a suitable culture medium inoculated with $10^6$ colony forming units of *Staphylococcus aureus* ATCC 25923 per ml. of said broth, containing not more than 0.06 ml of said oxidized limonene per ml. of said broth and incubated at 37° C. in air for 60 minutes.

2. The process of claim 1 wherein said rapid bactericidal activity remains substantially unchanged upon storage at 4° C. in a dark covered container for at least 6 months.

3. The process of claim 1 wherein said process consists essentially of bubbling air into limonene until said rapid bactericidal activity is reached.

4. The process of claim 1 wherein said process consists essentially of bubbling oxygen into limonene until said rapid bactericidal activity is reached.

5. The process of claim 3 wherein the said air is bubbled into limonene for about 3-8 weeks at room temperature.

6. The process of claim 4 wherein said oxygen is bubbled into limonene for about 3-8 weeks at room temperature.

7. A process for producing a stable microbicide which process consists essentially of bubbling air or oxygen into limonene to produce an oxidized limonene having a rapid bactericidal activity as evidenced by the capability of killing at least 99.99% of the bacteria in a suitable culture medium inoculated with $10^6$ colony forming units of *Staphylococcus aureus* ATCC 25923 per ml. of said broth, containing not more than 0.06 ml of said oxidized limonene per ml. of said broth and incubated at 37° C. in air for 60 minutes.

8. The process of claim 7 wherein said rapid bactericidal activity remains substantially unchanged upon storage at 4° C. in a dark covered container for at least 6 months.

9. The process of claim 7 wherein said process consists essentially of bubbling air into limonene until said rapid bactericidal activity is reached.

10. The process of claim 7 wherein said process consists essentially of bubbling oxygen into limonene until said rapid bactericidal activity is reached.

11. The process of claim 9 wherein the said air is bubbled into limonene for about 3-8 weeks at room temperature.

12. The process of claim 10 wherein said oxygen is bubbled into limonene for about 3-8 weeks at room temperature.

* * * * *